US009144382B2

(12) United States Patent
Nazarian et al.

(10) Patent No.: US 9,144,382 B2
(45) Date of Patent: Sep. 29, 2015

(54) NON-INVASIVE METHODS AND SYSTEMS FOR PRODUCING CARDIAC ELECTROGRAM CHARACTERISTIC MAPS FOR USE WITH CATHETER ABLATION OF VENTRICULAR TACHYCARDIA

(75) Inventors: Saman Nazarian, Baltimore, MD (US); Christopher Miller, Baltimore, MD (US); Takeshi Sasaki, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 1 day.

(21) Appl. No.: 14/009,755

(22) PCT Filed: Apr. 9, 2012

(86) PCT No.: PCT/US2012/032768
§ 371 (c)(1),
(2), (4) Date: Oct. 3, 2013

(87) PCT Pub. No.: WO2012/139116
PCT Pub. Date: Oct. 11, 2012

(65) Prior Publication Data
US 2014/0023256 A1    Jan. 23, 2014

Related U.S. Application Data

(60) Provisional application No. 61/472,699, filed on Apr. 7, 2011.

(51) Int. Cl.
*G06K 9/00* (2006.01)
*A61B 5/00* (2006.01)
(Continued)

(52) U.S. Cl.
CPC ............. *A61B 5/0044* (2013.01); *A61B 5/0402* (2013.01); *A61B 5/4836* (2013.01); *A61B 5/7203* (2013.01); *A61B 5/7278* (2013.01); *A61B 18/1492* (2013.01)

(58) Field of Classification Search
CPC ............. A61B 18/1492; A61B 5/0044; A61B 5/0402; A61B 5/4836; A61B 5/7203; A61B 5/02; A61B 5/055; A61B 5/7278; C07D 231/56; C07D 401/04; C07D 403/04; C07D 403/12; C07D 405/12; C07D 409/12; C07D 413/12; C07D 417/04
USPC .......................................... 382/128, 131, 154
See application file for complete search history.

(56) References Cited

U.S. PATENT DOCUMENTS

2002/0087089 A1   7/2002  Ben-Haim
2006/0253030 A1  11/2006  Altmann et al.
(Continued)

OTHER PUBLICATIONS

International Search Report and Written Opinion of PCT/US2012/032768.
(Continued)

*Primary Examiner* — Tom Y Lu
(74) *Attorney, Agent, or Firm* — Venable LLP; Henry J. Daley

(57) ABSTRACT

A non-invasive method of producing a three-dimensional cardiac electrogram characteristic map for use in catheter ablation of ventricular tachycardia includes receiving left ventricle three-dimensional image data of a patient's heart; segmenting a left ventricle image of the patient's heart based on the left ventricle three-dimensional image data into scar tissue, normal myocardium tissue and left ventricle cavity regions; determining scar tissue thickness and normal myocardium tissue thickness for a plurality of portions of the left ventricle image of the patient's heart; receiving predetermined data that associate a value of at least one electrogram characteristic to each scar tissue thickness and each normal myocardium tissue thickness for the plurality of portions of said left ventricle image of said patient's heart; and generating the three-dimensional cardiac electrogram characteristic map of the at least one electrogram characteristic corresponding to the left ventricle image of the patient's heart based on the predetermined data.

27 Claims, 6 Drawing Sheets

(51) Int. Cl.
A61B 5/0402 (2006.01)
A61B 18/14 (2006.01)

(56) References Cited

U.S. PATENT DOCUMENTS

| | | | |
|---|---|---|---|
| 2006/0263338 A1* | 11/2006 | Jacoby et al. | 424/93.7 |
| 2009/0161938 A1 | 6/2009 | Shekhar et al. | |
| 2010/0312096 A1 | 12/2010 | Guttman et al. | |
| 2013/0116789 A1* | 5/2013 | Chachques et al. | 623/14.13 |

OTHER PUBLICATIONS

Bertaglia et al., Integration of three-dimensional left atrial magnetic resonance images into a real-time electroanatomic mapping system: validation of a registration method. Pacing Clin Electrophysiol. 2008;31:273-282.

Bogun et al., Isolated potentials during sinus rhythm and pace-mapping within scars as guides for ablation of post-infarction ventricular tachycardia. J Am Coll Cardiol. 2006;47:2013-2019.

Brunckhorst et al., Relationship of Slow Conduction Detected by Pace-Mapping to Ventricular Tachycardia Re-Entry Circuit Sties After Infarction. J Am Coll Cardiol. 2003;41:802-809.

Chillou et al., Isthmus characteristics of reentrant ventricular tachycardia aftere myocardial infarction. Circulation.2002;105:726-731.

Codreanu et al., Electroanatomic characterization of post-infarct scars comparison with 3-dimensional myocardial scar reconstruction based on magnetic resonance imaging. J Am Coll Cardiol. 2008;52:839-842.

Desjardins et al., Infarct architecture and characteristics on delayed enhanced magnetic resonance imaging and electroanatomic mapping in patients with postinfarction ventricular arrhythmia. Heart Rhythm. 2009;6:644-651.

Dickfeld et al., Integration of three-dimensional scar maps for ventricular tachycardia ablation with positron emission tomography-computed tomography. JACC Cardiovasc Imaging. 2008;1:73-82.

Dickfeld et al., MRI-Guided Ventricular Tachycardia Ablation: Integration of Late Gadolinium-Enhanced 3D Scar in Patients With Implantable Cardioverter-Defibrillators. Circ Arrhythm Electrophysiol. 2011; 4:172-184.

Estner et al., The critical isthmus sites of ischemic ventricular tachycardia are in zones of tissue heterogeneity, visualized by magnetic resonance imaging. Heart Rhythm. 2011;8:1942-1949.

Hsia et al., Anatomic characterization of endocardial substrate for hemodynamically stable reentrant ventricular tachycardia: Identification of endocardial conducting channels. Heart Rhythm 2006;3:503-512.

Kim et al., Relationship of MRI delayed contrast enhancement to irreversible injury, infarct age, and contractile function. Circulation. 1999;100:1992-2002.

Marchlinski et al., Linear ablation lesions for control of unmappable ventricular tachycardia in patients with ischemic and nonischemic cardiomyopathy. Circulation. 2000;101:1288-1296.

Nazarian et al., Magnetic resonance assessment of the substrate for inducible ventricular tachycardia in nonischemic cardiomyopathy. Circulation. 2005;112:2821-5.

Nazarian et al., A prospective evaluation of a protocol for magnetic resonance imaging of patients with implanted cardiac devices. Ann Intern Med. 2011;155:415-24.

Nazarian et al., Clinical utility and safety of a protocol for noncardiac and cardiac magnetic resonance imaging of patients with permanent pacemakers and implantablecardioverter defibrillators at 1.5 tesla. Circulation. 2006;114:1277-1284.

Otomo et al., Local unipolar and bipolar electrogram criteria for evaluating the transmurality of atrial ablation lesions at different catheter orientation relative to the endocardial surface. Heart Rhythm. 2010;7:1291-1300.

Perez-David et al., Noninvasive identification of ventricular tachycardia-related conducting channels using contrast-enhanced magnetic resonance imaging in patients with chronic myocardial infarction: comparison of signal intensity scar mapping and endocardial voltage mapping.J Am Coll Cardiol. 2011;57:184-194.

Perin et al., Assessing myocardial viability and infarct transmurality with left ventricular electromechanical mapping in patients with stable coronary artery disease: validation by delayed-enhancement magnetic resonance imaging. Circulation. 2002;106:957-961.

Psaltis et al., Assessment of myocardial fibrosis by endoventricular electromechanical mapping in experimental nonischemic cardiomyopathy. Int J Cardiovasc Imaging. 2011;27:25-37.

Reddy et al., Combined epicardial and endocardial electroanatomic mapping in a porcine model of healed myocardial infarction. Circulation. 2003;107:3236-3242.

Roes et al., Infarct tissue heterogeneity assessed with contrast-enhanced MRI predicts spontaneous ventricular arrhythmia in patients with ischemic cardiomyopathy and implantable cardioverter-defibrillator. Circ Cardiovasc Imaging. 2009;2:183-190.

Sasaki et al., Quantitative assessment of artifacts on cardiac magnetic resonance imaging of patients with pacemakers and implantable cardioverter-defibrillators, Circ Cardiovasc Imaging. 2011;4:662-70.

Setser et al., Quantitative assessment of myocardial scar in delayed enhancement magnetic resonance imaging. J Magn Reson Imaging. 2003;18:434-441.

Stevenson et al., Identification of reentry circuit sites during catheter mapping and radiofrequency ablation of ventricular tachycardia late after myocardial infarction.Circulation. 1993;88:1647-70.

Stevenson et al., Relation of pace mapping QRS configuration and conduction delay to ventricular tachycardia reentry circuits in human infarct scars. J Am Coll Cardiol 1995;26:481-488.

Tung et al., Distinguishing epicardial fat from scar: Analysis of electrograms using high-density electroanatomic mapping in a novel porcine infarct model. Heart Rhythm. 2010;7:389-395.

Wijnmaalen et al., Head-to-head comparison of contrast-enhanced magnetic resonance imaging and electroanatomical voltage mapping to assess post-infarct scar characteristics in patients with ventricular tachycardias: real-time image integration and reversed registration. Eur Heart J. 2011;32:104-114.

Wolf et al., Detailed endocardial mapping accurately predicts the transmural extent of myocardial infarction. J Am Coll Cardiol. 2001;37:1590-1597.

Zeppenfeld et al., Identification of successful catheter ablation sites in patients with ventricular tachycardia based on electrogram characteristics during sinus rhythm. Heart Rhythm. 2005;2:940-50.

* cited by examiner

NON-INVASIVE METHODS AND SYSTEMS FOR PRODUCING CARDIAC ELECTROGRAM CHARACTERISTIC MAPS FOR USE WITH CATHETER ABLATION OF VENTRICULAR TACHYCARDIA

CROSS-REFERENCE OF RELATED APPLICATION

This is a national stage application under 35 U.S.C. §371 of PCT/US2012/032768 filed Apr. 9, 2012, the entire contents of which are incorporated herein by reference and this application claims priority to U.S. Provisional Application No. 61/472,699 filed Apr. 7, 2011, the entire contents of which are hereby incorporated by reference.

This invention was made with U.S. Government support of Grant No. K23HL089333, awarded by NIH. The U.S. Government has certain rights in this invention.

BACKGROUND

1. Field of Invention

The field of the currently claimed embodiments of this invention relates to non-invasive methods and systems of producing cardiac electrogram characteristic maps for use in catheter ablation of ventricular tachycardia.

2. Discussion of Related Art

Radiofrequency catheter ablation is increasingly used as an adjunct to implantable cardioverter defibrillators (ICD) and medical therapy for management of scar-related ventricular tachycardia (VT) in patients with ischemic and nonischemic cardiomyopathy.[1-9] Due to hemodynamic instability, the majority of scar-related VTs are unmappable during tachycardia. Consequently, significant progress has been made in substrate-guided VT ablation based on electrogram (EGM) characteristics as surrogates of the scar substrate on electroanatomic maps (EAMs) obtained during sinus rhythm or ventricular pacing. The EGM characteristics central to identification of tissues that participate in VT circuits include low bipolar and unipolar EGM voltage and fractionated or isolated potentials. However, creation of invasive EAM significantly prolongs procedural time, and is limited by sampling density.

Late gadolinium enhancement (LGE) on cardiac magnetic resonance (CMR) can accurately characterize the transmural extent, location, and configuration of scar.[10-11] Previous reports have shown that scar extent on LGE-CMR is significantly associated with left ventricular dysfunction, VT inducibility, and prognosis in patients with structural heart disease.[12,13] Additionally, scar transmurality, defined as the ratio of post-infarct scar thickness (PI-ST) to left ventricular wall thickness (LV-WT), has been associated with EGM characteristics on EAM.[14-22] However, the independent association of LV-WT and PI-ST with EGM characteristics has not been investigated, and no models exist for quantitative estimation of local EGM characteristics based on LGE-CMR. Scar maps can be directly imported into the procedure; however, the extent of scar transmurality and surviving muscle fibers (i.e. heterogeneity of tissues) are difficult to display. Accurate methods for extraction of critical image features are mandatory for acceptance of magnetic resonance guided catheter ablation. There thus remains a need for improved non-invasive methods and systems of producing cardiac electrogram characteristic maps for use in catheter ablation of ventricular tachycardia.

SUMMARY

A non-invasive method of producing a three-dimensional cardiac electrogram characteristic map for use in catheter ablation of ventricular tachycardia according to an embodiment of the current invention includes receiving left ventricle three-dimensional image data of a patient's heart; segmenting a left ventricle image of the patient's heart based on the left ventricle three-dimensional image data into scar tissue, normal myocardium tissue and left ventricle cavity regions; determining scar tissue thickness and normal myocardium tissue thickness for a plurality of portions of the left ventricle image of the patient's heart; receiving predetermined data that associate a value of at least one electrogram characteristic to each scar tissue thickness and each normal myocardium tissue thickness for the plurality of portions of said left ventricle image of said patient's heart; and generating the three-dimensional cardiac electrogram characteristic map of the at least one electrogram characteristic corresponding to the left ventricle image of the patient's heart based on the predetermined data.

A computer-readable medium according to an embodiment of the current invention includes computer-executable code for producing a three-dimensional cardiac electrogram characteristic map for use in catheter ablation of ventricular tachycardia. The computer-executable code includes instructions that, when executed by the computer, causes said computer to receive left ventricle three-dimensional image data of a patient's heart; segment a left ventricle image of the patient's heart based on the left ventricle three-dimensional image data into scar tissue, normal myocardium tissue and left ventricle cavity regions; determine scar tissue thickness and normal myocardium tissue thickness for a plurality of portions of the left ventricle image of the patient's heart; receive predetermined data that associate a value of at least one electrogram characteristic to each scar tissue thickness and each normal myocardium tissue thickness for the plurality of portions of the left ventricle image of the patient's heart; and render a three-dimensional cardiac electrogram characteristic map of the at least one electrogram characteristic corresponding to the left ventricle image of the patient's heart based on the predetermined data.

A system for producing a three-dimensional cardiac electrogram characteristic map for use in catheter ablation of ventricular tachycardia according to an embodiment of the current invention includes a data processing unit and a data storage unit configured to communicate with the data storage unit. The data processing unit is configured to execute instructions that causes the system to receive left ventricle three-dimensional image data of a patient's heart; segment a left ventricle image of the patient's heart based on the left ventricle three-dimensional image data into scar tissue, normal myocardium tissue and left ventricle cavity regions; determine scar tissue thickness and normal myocardium tissue thickness for a plurality of portions of the left ventricle image of the patient's heart; receive predetermined data that associate a value of at least one electrogram characteristic to each scar tissue thickness and each normal myocardium tissue thickness for the plurality of portions of the left ventricle image of the patient's heart; and render a three-dimensional cardiac electrogram characteristic map of the at least one electrogram characteristic corresponding to the left ventricle image of the patient's heart based on the predetermined data.

BRIEF DESCRIPTION OF THE DRAWINGS

Further objectives and advantages will become apparent from a consideration of the description, drawings, and examples.

DETAILED DESCRIPTION

Figure 1:
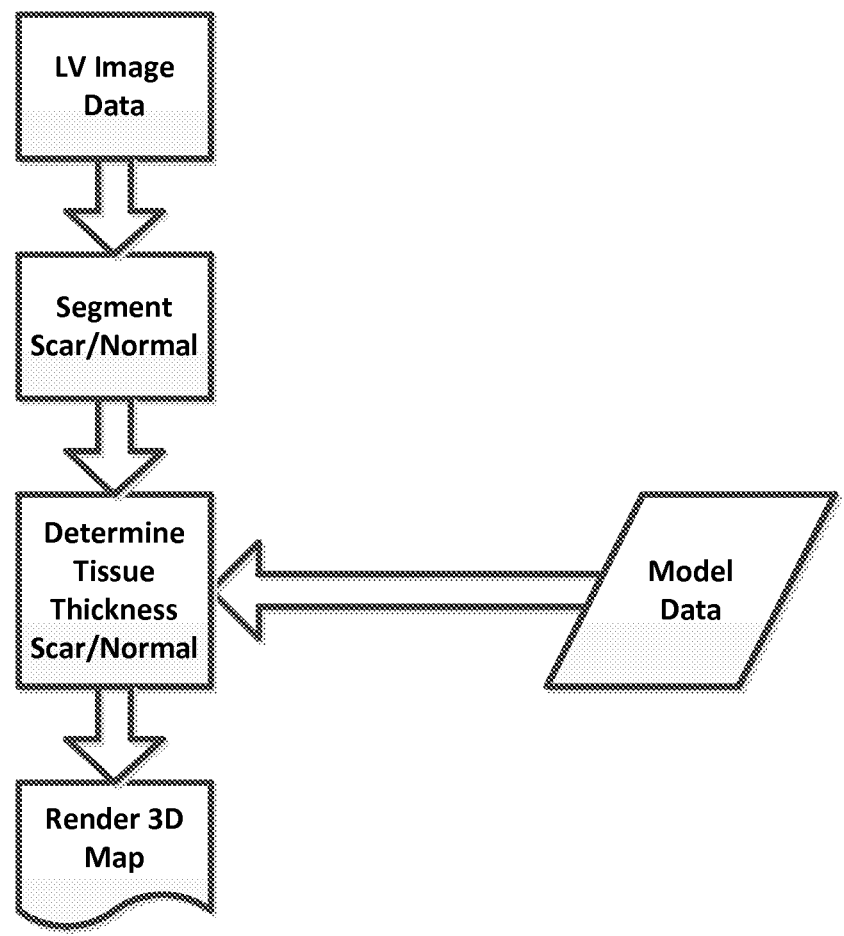
FIG. 1 is a flow chart to help explain methods of producing cardiac electrogram characteristic maps for use in catheter ablation of ventricular tachycardia according to some embodiments of the current invention.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Ventricular Tachycardia (VT) is a significant contributor to morbidity and mortality in patients with ischemic and non-ischemic cardiomyopathy. In this setting, VT is mechanistically a result of reentry or the propagation of activation around scar. Catheter ablation aims to cure VT by permanently interrupting conduction in a critical portion of such a reentrant circuit. Failure of catheter ablation occurs in >35% of cases and is often attributed to hemodynamic instability of the VT which precludes a detailed study of the VT circuit. If the complete sequence of activation is unattainable, the electrophysiologist must focus his/her attention on areas of the heart that are likely to contain the critical portion of the reentry circuit. To identify such candidate areas, catheter ablation of ischemic VT begins by an attempt to map the myocardial substrate by creation of an endocardial voltage map. Electro-anatomic systems use positional sensors on the catheter tip and the voltage from each sampled point to create 3-dimensional maps with a color scale that describes the range of voltage from healthy (>1.5 mV) to dense scar (<0.5 mV). Such invasively created voltage maps, however, have several disadvantages: First, map creation is time consuming and complications are directly associated with procedure length. Second, current electro-anatomic systems extrapolate the voltage of missing areas (by averaging of neighboring sites) and the sampling density is directly proportional to map accuracy. Third, poor catheter contact can dramatically alter map accuracy. We have performed extensive work on the association between cardiac magnetic resonance (CMR) scar images and regional myocardial voltage. This work has enabled the creation of multivariate regression equations that can predict the voltage at each imaging sector, and non-invasively create voltage maps unique to each individual.

The availability of a pre-procedural non-invasive voltage map can offer several potential advantages: First, time that would otherwise be used (during the catheter ablation procedure) to create the map can be devoted to selection and ablation of critical VT sites. Second, all map areas would be derived from cardiac MRI images and no points would be extrapolated by averaging information from invasively sampled points. Third, map accuracy would not be affected by catheter contact.

The entire map can be created based upon cardiac MRI imaging according to some embodiments of the current invention. However, the broad concepts of the current invention are not limited to only the use of MRI. Other imaging modalities, such as, but not limited to, CT imaging, can also be used in other embodiments of the current invention. A strategy for ablation could be developed prior to introducing any catheters into the body. Non-invasive voltage (and other electrogram characteristic) maps for the purpose of catheter ablation have never before been created prior to such procedures.

An aspect of the current invention concerns the development of predictive models for anatomic non-invasive voltage map creation based upon Late Gadolinium Enhancement Cardiac Magnetic Resonance (LGE-CMR) images. This approach can be summarized, as follows. Multivariate regression models in an example according to an embodiment of the current invention were based upon retrospective data from 10 prior ventricular tachycardia ablation procedures. Left ventricular wall thickness (LVWT) and scar transmurality were measured in short axis planes of LGE-CMR prior to VT ablation in patients with ischemic cardiomyopathy. Post infarct scar thickness (PIST) was calculated by the multiplication of scar transmurality and wall thickness. Substrate maps during sinus rhythm were then obtained with an electroanatomic mapping system (Carto; Biosense Webster, Diamond Bar, Calif.) during VT ablation. Invasively sampled mapping points were retrospectively registered to the corresponding 1712 sectors on LGE-CMR by custom software. Multilevel (clustered by patient) multivariate linear regression analyses revealed a significant association between LGE CMR derived variables and electrogram characteristics. The models revealed a significant association between scar/wall thickness and bipolar and unipolar electrogram amplitudes. The comparison of electrogram duration and deflection (fractionation) with scar transmurality also revealed a statistically significant direct association. In addition, there were significant direct associations between the incidence of fractionated and isolated delayed potentials and scar transmurality.

In some particular examples according to an embodiment of the current invention, the multivariate regression models were then used in custom software to non-invasively predict the voltage map based upon MRI Images. Comparison of invasive to non-invasive maps has revealed very close results.

It is expected that this methodology and/or software according to some embodiments of the current invention can be used for creation of non-invasive voltage maps prior to every ventricular tachycardia catheter ablation procedure, for example. For example, some embodiments of the current invention can provide software modules that can be used in electroanatomic mapping systems.

FIG. 1 is a flowchart to help illustrate a non-invasive method of producing a three-dimensional cardiac electrogram characteristic map for use in catheter ablation of ventricular tachycardia according to an embodiment of the current invention. The electrogram characteristic can be, but is not limited to, at least one of bipolar voltage amplitude, unipolar voltage amplitude, electrogram deflection, electrogram fractionation, or electrogram duration, for example.

The method according to this embodiment includes receiving at least left ventricle three-dimensional image data of a patient's heart. The image data can be magnetic resonance image (MRI) data according to an embodiment of the current invention. For example, the MRI data can be late gadolinium enhancement on cardiac magnetic resonance data according to an embodiment of the current invention. In another embodiment of the current invention, the image data can be x-ray computed tomography (CT) data. In some embodiments, the CT data can be late enhanced or perfusion CT data, for example. However, the broad concepts of the current invention are not limited to these particular examples. Other non-invasive imaging modalities can be used as long as they can provide the structural information that is used in the modeling and mapping.

The method according to this embodiment of the current invention also includes segmenting a left ventricle image of the patient's heart that is provided by the left ventricle three-dimensional image data into scar tissue regions, normal myocardium tissue regions and left ventricle cavity regions. Then, scar tissue thickness and normal myocardium tissue thickness is determined for a plurality of portions of the left ventricle image of the patient's heart. For example, the LV image can be broken up into triangular mesh elements, or any other suitable elements. Further, the general concepts of the current invention are not limited to a particular resolution of these segments.

Next, predetermined data that associates a value of at least one electrogram characteristic to each scar tissue thickness and each normal myocardium tissue thickness for the plurality of portions of the left ventricle image of the patient's heart is received. The predetermined data can be model data for example. The model data can be an empirical model according to some embodiments of the current invention. For example, the predetermined data can be, but is not limited to, coefficients determined from a multi-level, multivariate linear regression analysis of empirical data.

The method according to this embodiment of the current invention further includes generating the three-dimensional cardiac electrogram characteristic map of the at least one electrogram characteristic corresponding to the left ventricle image of the patient's heart based on the predetermined data. For example, one or more such three-dimensional cardiac electrogram characteristic maps can be displayed on a display screen along with an image indicating the location of the ablation catheter during an ablation procedure.

The method according to some embodiments of the current invention can further include receiving patient characteristic data and also using the patient characteristic data while generating the three-dimensional cardiac electrogram characteristic map. The patient characteristic data can include, but is not limited to, at least one of age, gender, body mass index, history of coronary artery bypass grafting, or history of use of antiarrhythmic drugs. The method according to other embodiments of the current invention can further include determining left ventricle fraction ejection of the patient based on the left ventricle three-dimensional image data and also use such data while generating the three-dimensional cardiac electrogram characteristic map.

In some embodiments of the current invention, computer-executable code stored can be stored in computer readable media such that when the code is executed, it performs a method according to an embodiment of the current invention. The code can be stored in a non-transitory medium, for example. In other embodiments, a system can be configured to perform the method according to an embodiment of the current invention. The system can be configured by hard wiring and/or through software to perform a method according to an embodiment of the current invention. The system can be, or can include, a computer, for example. The system can also be an ablation system than include a data processor and a data storage system, for example.

EXAMPLES

The following examples are provided to help explain further concepts and details of some embodiments of the current invention. However, the general concepts of the current invention are not limited to the particular examples.

Methods

Study Patients

LGE-CMR images were acquired in 23 patients (23 males, 68±8 years old) with ischemic cardiomyopathy and scar-related VT prior to catheter ablation. The first 13 patients formed the retrospective training set for development of multivariate models, and the subsequent 10 patients formed the prospective test set for model validation. Catheter ablation was performed for recurrent ICD shocks or prior to ICD implantation for secondary prevention of VT.

CMR Studies

CMR was performed with a 1.5T magnetic resonance scanner (Avanto, Siemens, Erlangen, Germany). In patients with ICD systems, potential risks of exposure to magnetic fields were explained before CMR scans, and CMR images were obtained using our established safety protocol.[23-25] ECG telemetry, pulse oximetry, blood pressure and symptoms were monitored during CMR. Cine steady-state free precession gradient-echo images (Cine-CMR) were obtained in short axis planes (echo time 1.1-1.6 ms, repetition time 2.5-3.8 ms, average in-plane resolution 1.4×1.4 mm; flip angle 15-60°; temporal resolution 40-45 ms) in contiguous 8 mm short axis planes from base to apex. Next, 0.2 mmol/kg gadodiamide was administered intravenously at a rate of 2 ml/sec followed by a 20 cc saline flush. Fifteen minutes after the injection of the contrast medium, LGE-CMR images were obtained in short axis with an inversion-recovery fast-gradient-echo pulse sequence (echo time 1.3-3.9 ms, repetition time 5.4-8.3 ms, average in-plane resolution 1.5×2.0 mm; 8 mm slice thickness). Inversion times (range 175-300 ms) were optimized for each patient to maximize conspicuity of myocardial areas with delayed enhancement. Single planes of LGE-CMR were also acquired in horizontal and vertical long axis planes to confirm the existence of enhancement in at least 2 planes.

CMR Image Analysis

Figures 2A, 2B, 2C, 2D:
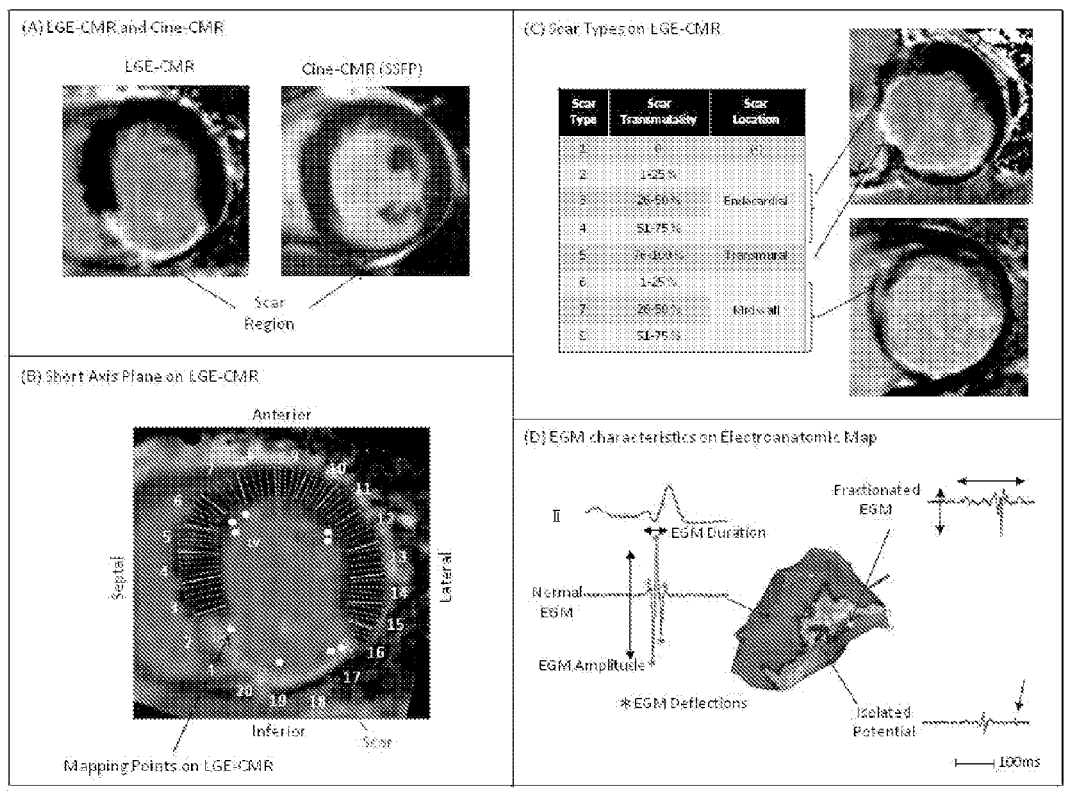
FIG. 2A shows an example of scar that was identified by late gadolinium enhancement cardiac magnetic resonance (LGE-CMR). Scar and Myocardial wall thickness were determined by both LGE-CMR and steady state free procession imaging (Cine-CMR).
FIG. 2B shows mapping points on electroanatomic maps (EAM) that were registered to the corresponding region on short axis planes of LGE-CMR.
FIG. 2C shows scar on LGE-CMR that was divided into 8 types by scar transmurality (0-25, 26-50, 51-75, 76-100%) and intramural scar location (normal, endocardial, mid wall, transmural).
FIG. 2D shows EGM characteristics on EAM that were defined as EGM parameters (bipolar and unipolar EGM voltages, duration, deflection) and EGM types (normal, fractionated EGM, isolated potential, abnormal EGM).

QMass® MR software (General Electric Healthcare Technologies, Leiden, Netherlands) was used to measure scar transmurality and LV-WT. The LV endocardium and epicardium were contoured manually in every short axis plane on LGE-CMR. To measure LV-WT accurately, both contours were determined in comparison with those in the corresponding short axis plane on Cine-CMR (FIG. 2A). Candidate hyperenhanced regions were identified as scar if the mean intensity of the hyperenhanced region was >3 standard deviations above the mean intensity of remote normal myocardium region without hyperenhancement. Each short axis plane of LGE-CMR was divided into 20 radial sectors. In each sector, 4 radial lines were drawn from epicardium to endocardium and the proportion of each line that intersected scar was calculated.[13] Scar transmurality was defined as the average scar transmurality of all lines per sector (FIG. 2B). LV-WT was measured in the same manner as transmurality. LV-WT was defined as the average wall thickness of all lines per sector on short plane of LGE-CMR. FI-ST was calculated by the multiplication of scar transmurality and wall thickness. Scar on LGE-CMR was classified by scar transmurality (0%, 1-25%, 26-50%, 51-75%, 76-100%) and intramural scar location (endocardial, transmural, mid wall) (FIG. 2C).

Electrophysiological Study

In patients with ICD or biventricular ICD, the back-up pacing rate was set at 50 pulses per minutes and tachyarrhythmia therapies were disabled prior to the procedure. Three quadripolar catheters were inserted via the femoral vein and advanced to the high right atrium, right ventricle, and the His bundle region. Ventricular programmed-stimulation to induce VT was performed from the RV apex and RV outflow tract with up to triple extrastimuli at three basic cycle lengths. If the induced VT sustained without hemodynamic collapse, LV mapping was attempted during the tachycardia. Otherwise, substrate mapping was performed during sinus rhythm. After the insertion of the mapping catheter into the arterial circulation, sufficient heparin was administered to maintain an activated clotting time of >300 seconds.

3D Electroanatomic Maps and Electrogram Characteristics

A 3D electroanatomic mapping system (CARTO, Biosense Webster, Inc., Diamond Bar, Calif.) was used to create endocardial voltage maps of the left ventricle (LV) during sinus rhythm using a 3.5 mm-tip electrode (Thermocool, Biosense Webster, Inc.). The "Fill Threshold" of the EAM on CARTO system was set at 15 mm. The mapping catheter was inserted into the left ventricle (LV) using a transseptal approach in all patients. The LV shell reconstructed from the CMR angiogram was registered to the LV EAM using the landmark registration method on the CARTO system. LV apex, mitral annulus and aortic annulus or RV septal insertions were selected as three LV landmarks. Additional EAMs were created in the right ventricle (RV) or aorta to minimize rotational error. After landmark registration, surface registration was performed. The accuracy of those registrations were determined using statistical summation on the CARTO system, which is the average distance of the each EAM point to the closest surface point of the reconstructed LV shell.[26] Local bipolar and unipolar EGM voltage, duration and deflection were assessed as EGM parameters on EAM. Bipolar and unipolar EGMs were filtered at 10-400 Hz and 1-240 Hz, respectively, and both voltage measures were recorded as the difference between the highest and lowest deflections of a stable contact signal. EGM duration and deflection were measured from the onset to the end of the EGM deflections at 400 mm/s speed manually. The number of deflections was counted as the summation of both negative and positive deflections in each EGM (FIG. 1d).[27,28] Bipolar EGMs recorded by the distal electrodes of the mapping catheter were also categorized based on criteria used in previous reports[6-9,29] as normal, fractionated, isolated potential, and abnormal EGM. 1) Normal EGM: sharp biphasic or triphasic spikes with voltage amplitudes mV and duration <70 ms, and/or amplitude/duration ratio>0.046 2) Fractionated EGM: amplitude 0.5 mV, duration 133 ms, and/or amplitude/duration ratio<0.005, 3) Isolated potential: a potential separated from the ventricular EGM by an isoelectric segment, and/or a segment with low voltage noise (<0.05 mV) of >20 ms duration at a gain of 40 to 80 mm/mV, 4) The other EGMs were defined as abnormal EGMs.[29] These EGM characteristics were analyzed by two independent observers. The discrepancies (<10) were resolved by repeat review by a third observer and consensus among all reviewers. In accepting the EGM in each EAM point, we confirmed that at least 2 consecutive EGMs had the same morphology to avoid EGM artifact due to poor catheter contact.

Catheter Ablation of Scar-Related Ventricular Tachycardia

Radiofrequency catheter ablations were performed during sinus rhythm or hemodynamically stable VT using a 3.5-mm tip open-irrigation catheter (ThermoCool, Biosense Webster, Diamond Bar, Calif.). Ablation targets were principally determined by pace mapping during sinus rhythm and entrainment mapping during sustained monomorphic VT. Additional radiofrequency applications were also performed targeting fractionated and isolated potentials within scar, or connecting scar to the closest electrically non-conducting structure (mitral valve annulus).[1-9,14-19] The critical sites of scar-related reentrant VT were defined as sites with low voltage and 12/12 ECG morphology match to VT during pacing, or concealed entrainment and post pacing interval-VT cycle length <30 msec identified during hemodynamically stable VT. These critical sites were then categorized as exit, central pathway, or entrance sites by determination of the ratio of stimulus to QRS time divided by the VT cycle length (% S-QRS/VT-CL; Exit <30%, Central pathway 30-70%, entrance 70%>).[1,2] Radiofrequency energy was delivered with maximum power of 40 W for 30-60 seconds at each target site. Programmed stimulation with 3 extrastimuli was performed at the end of each procedure to confirm acute success. The endpoint of substrate-guided ablation was complete non-inducibility of clinical tachycardia. Complete success was defined as non inducibility of any VT. Partial success was defined as suppression of the clinical VT but inducibility of any other VT. Device interrogation was performed in all patients with ICD or biventricular ICD immediately after the ablation procedure, and devices were reprogrammed to original settings.

Registration of EAM Points to LGE-CMR Images

The LGE-CMR images were retrospectively registered to the endocardial 3D EAM using custom software (Volley, Johns Hopkins University) based on the registration coordinates for EAM merge with the LV CMR angiogram.[7] Each EAM point was superimposed onto the corresponding region on short axis LGE-CMR image planes. EGM characteristics corresponding to each image sector on LGE-CMR were recorded as continuous variables.

Statistical Analysis

Continuous variables are expressed as mean±SD and categorical data as numbers or percentages. Comparisons of continuous variables regarding each EGM parameter were made using ANOVA or a nonparametric test based on the distribution of the values. The association of EGM types (normal, abnormal, fractionated and isolatedpotential) on EAM with scar types (FIG. 2D) was investigated by the chi-squared test. Multi-level multivariate linear regression models with EGM parameters as dependent variables and LV-WT, PI-ST, myocardial location (anterior, septal, inferior, lateral), and intramural scar location (endocardial, mid wall, transmural) at each sampled point as independent variables, clustered by patient and adjusting for patient characteristics (age, body mass index, LV ejection fraction, history of coronary artery bypass grafting and use of antiarrhythmic drugs) were created using the retrospective training set data. For patients assigned to the prospective test set, scar, normal myocardium and LV cavity were manually segmented in each short axis plane of LGE-CMR. The values of LV-WT and PI-ST were then measured in each of 360 equally spaced lines per short axis plane drawn from the center of the LV to LV myocardium. Based on the measured LV-WT and PI-ST and the coefficients from multivariate linear regression analysis on the training set, we then calculated bipolar and unipolar voltage, duration, and deflections. The custom software (Volley, Johns Hopkins University)[7] then displayed each EGM measure on corresponding 3D maps with colors representing the full range of measured data for each EGM parameter. The associations of the measured data from invasive EAM and predicted data from non-invasive 3D maps were assessed by spearman's correlation test. The correlations between stimulus to QRS time (S-QRS) or % S-QRS/VT-CL and scar transmurality were also assessed by spearman's correlation test. Statistical analyses were performed using STATA software (version 10, StataCorp, College Station, Tex.).

Results

Patients Characteristics

All 23 patients were male and the mean age was 68±8 years. Other baseline characteristics have been summarized in Table 1. Fifteen patients had ICD or biventricular ICD systems at the time of MRI scans. All CMR scans were performed safely with our implantable device-MRI safety protocol.[23,24] In addition to standard therapy for heart failure, antiarrhythmic drugs (amiodarone and sotalol) had been administrated in 18 patients (78.3%). Antiarrhythmic drugs were discontinued at least 3 days prior to VT ablation.

TABLE 1

Patient Characteristics

| | All N = 23 | Retrospective Training Set N = 13 | Prospective Test Set N = 10 |
|---|---|---|---|
| Age [years] | 68 ± 8 | 68 ± 9 | 67 ± 7 |
| Gender Male/Female | 23/0 | 13/0 | 10/0 |
| BMI [kg/m2] | 26.9 ± 5.5 | 27.5 ± 6.8 | 26.1 ± 3.4 |
| HBP/DLP/DM/smoking | 17/12/4/12 | 10/6/3/6 | 7/6/1/4 |
| History of CABG | 10 | 5 | 5 |
| Myocardial Infarction | | | |
| Anteroseptal/Inferior/lateral/Broad | 7/12/2/2 | 4/6/1/2 | 3/6/1/0 |
| Ventricular Tachycardia (VT) | | | |
| Stable/Unstable | 8/15 | 4/9 | 4/6 |
| Monomorphic/Pleomorphic | 9/14 | 5/8 | 4/6 |
| Use of Antiarrhythmic Drug | | | |
| None/Amiodarone/Sotalol | 5/15/3 | 2/9/2 | 3/6/1 |
| MRI with In-situ ICD | 15 | 9 | 6 |
| ICD/BiV-ICD | 12/3 | 7/2 | 5/1 |
| Echocardiography | | | |
| Ejection Fraction [%] | 34 ± 16 | 34 ± 16 | 34 ± 9 |
| Left Ventricular Diastolic Diameter | 55 ± 9 | 57 ± 6 | 53 ± 12 |
| MRI | | | |
| LV End-diastolic volume [ml] | 271 ± 108 | 289 ± 92 | 250 ± 128 |
| LV End-systolic volume [ml] | 189 ± 99 | 196 ± 83 | 180 ± 121 |
| LV Stroke Volume [ml/beat] | 83 ± 20 | 93 ± 15 | 73 ± 19 |
| LV Cardiac Output [ml/minute] | 5.1 ± 1.5 | 5.5 ± 1.0 | 4.7 ± 1.8 |
| LV Ejection Fraction [%] | 33 ± 11 | 33 ± 8 | 32 ± 15 |

Values are expressed as mean ± SD or number.
BMI = body mass index;
HBP = high blood pressure;
DLP = dyslipidemia;
DM = diabetes mellitus;
CABG = coronary artery bypass grafting;
ICD = implantable cardioverter defibrillator;
LV = left ventricle.

Analyzed Sectors on LGE-CMR and EAM Points

A total of 3576 sectors in 189 short axis LGE-CMR planes of 23 patients' MRI examinations were reviewed. Of these, 2690 sectors (75.2%) were available for quantitative analysis. The remaining 24.8% of sectors were excluded from quantitative analysis due to MRI susceptibility artifacts in patients with ICD or biventricular ICD systems. Of 4315 EAM points, 2222 EAM points had to be excluded from the analysis due to the MRI artifacts in corresponding image sectors or evidence of suboptimal catheter contact. Consequently, 2093 EAM points obtained from the LV during sinus rhythm were retrospectively merged with the 2690 analyzable imaging sectors on LGE-CMR. The transmurality and location of scar on all LGE-CMR sectors and those sectors corresponding to sampled points on EAM in the retrospective training and the prospective test sets are summarized in Supplemental Table 1. Compared to the number of sectors with endocardial and transmural scar, mid-wall scar was not frequently observed because this form of scar is rare in ischemic cardiomyopathy.[10,11,16] Low voltage and dense scar areas defined as <1.5 mV and <0.5 mV of bipolar voltage covered 29.4% and 6.2% of total LV endocardium on EAM. The LV shells segmented from CMR angiogram were successfully merged with the endocardial LV EAM with a mean surface registration error of 2.8±0.7 mm. Details of electroanatomic mapping and catheter ablation are shown in Table 2. Complete success was attained in 10 and partial success in 13 patients. In 2 patients, worsening of heart failure with necessity of inpatient diuresis was recognized as a complication associated with the ablation procedures.

TABLE 2

Results of Electroanatomic Mapping and Catheter Ablation

|  | ALL (N = 23) | Retrospective Training Set (N = 13) | Prospective Test Set (N = 10) |
| --- | --- | --- | --- |
| Analyzed EAM Points | 2093 | 1293 | 800 |
| Low Voltage Area [cm²] | 58.2 ± 41.8 | 55.9 ± 36.3 | 61.1 ± 49.9 |
| (% for LV Endocardium) | (29.4 ± 21.6) | (27.6 ± 16.3) | (30.7 ± 27.2) |
| Dense Scar [cm²] | 13.9 ± 14.4 | 11.9 ± 7.1 | 16.9 ± 20.5 |
| (% for LV Endocardium) | (6.2 ± 5.3) | (5.0 ± 2.8) | (8.1 ± 7.4) |
| Surface Registration Error | 2.8 ± 0.7 | 3.0 ± 0.8 | 2.5 ± 0.5 |
| Number of Induced VT | 2.4 ± 1.3 | 2.4 ± 1.3 | 2.2 ± 1.1 |
| Number of RF Application | 20 ± 11 | 20 ± 12 | 20 ± 11 |
| Critical Sites | 39 sites (23 patients) | 20 sites (13 patients) | 19 sites (10 patients) |
| 12/12 Pace Map | 39 (100%) | 20 (100%) | 19 (100%) |
| PPI-VTCL <30 ms | 9 (23.1%) | 4 (20%) | 5 (26.3%) |
| Concealed Entrainment | 7 (18%) | 3 (15%) | 5 (26.3%) |
| Complete Success/Partial Success | 10/13 | 5/8 | 5/5 |
| Procedure Time [min] | 386 ± 65 | 394 ± 77 | 376 ± 48 |
| Fluoroscopy Time [min] | 76 ± 22 | 79 ± 24 | 71 ± 21 |
| Ablation Time [min] | 20 ± 12 | 19 ± 10 | 21 ± 15 |

Values are shown as number (%).
Low voltage area and dense scar on electroanatomic map (EAM) were defined as the areas with <1.5 mV and <0.5 mV of bipolar voltages, respectively.
RF = radiofrequency;
PPI-VTCL = post pacing interval-VT cycle length.
See abbreviations in Table 1.

Comparison of EGM Characteristics and Scar Transmurality

Figures 3A, 3B, 3C, 3D, 3E:
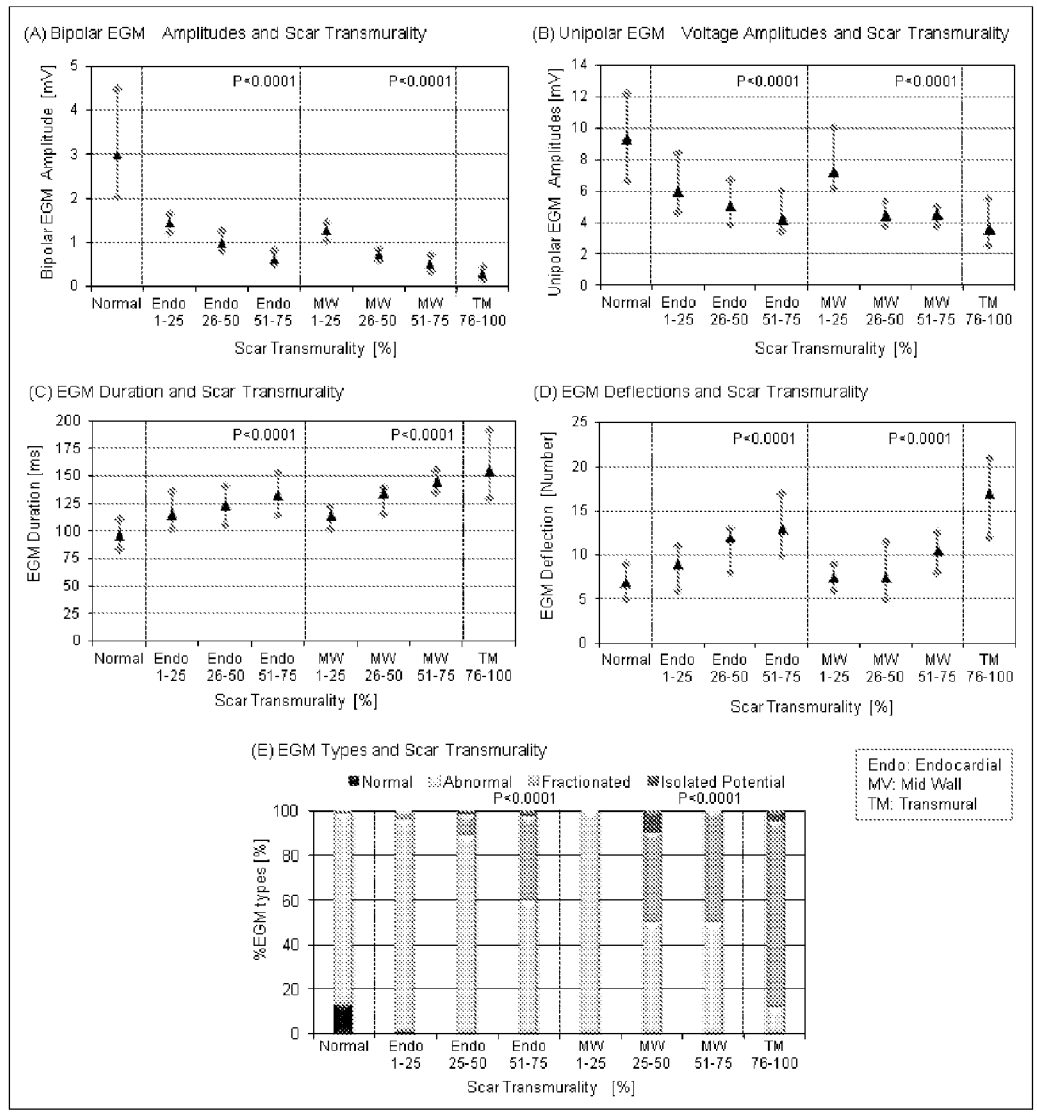
FIGS. 3A-3E illustrate the association of EGM parameters or EGM types with scar transmurality. (A) Bipolar and unipolar EGM voltage amplitudes were indirectly associated with endocardial ($P<0.0001$, test for trend) and mid wall scar transmurality ($P<0.0001$, test for trend). (B) EGM duration and deflections were indirectly associated with endocardial ($P<0.0001$, test for trend) and mid wall scar transmurality ($P<0.0001$, test for trend). The Box plots show the interquartile range (grey bar) and the median (black triangle). (C) Fractionated and isolated potential were more frequently observed in scar regions with greater scar transmurality ($P<0.0001$, test for trend).

The mean bipolar voltage and EGM duration were 3.0±2.3 mV and 96.5±27.0 ms, respectively, in myocardial areas without evidence of scar. In areas with scar, bipolar and unipolar EGM voltages were inversely associated with endocardial and mid wall scar transmurality (P<0.0001 test for trend, respectively; FIGS. 3A, 3B). EGM duration and deflections were also positively associated with endocardial and mid wall scar transmurality (P<0.0001 test for trend, respectively; FIGS. 3C, 3D). Of all EAM points analyzed, 6.1% had normal EGMs, 29.1% had fractionated EGMs, 3.1% had isolated potentials and 61.7% had abnormal EGMs. There was a direct association between the incidence of fractionated EGM and isolated potentials with endocardial and mid wall scar transmurality (P<0.0001 test for trend, respectively; FIG. 3E). Fractionated EGMs and isolated potentials were more frequently observed in regions with higher scar transmurality.

Comparison of Critical Ablation Sites and Intramural Scar Location

Figures 4A, 4B, 4C, 4D:
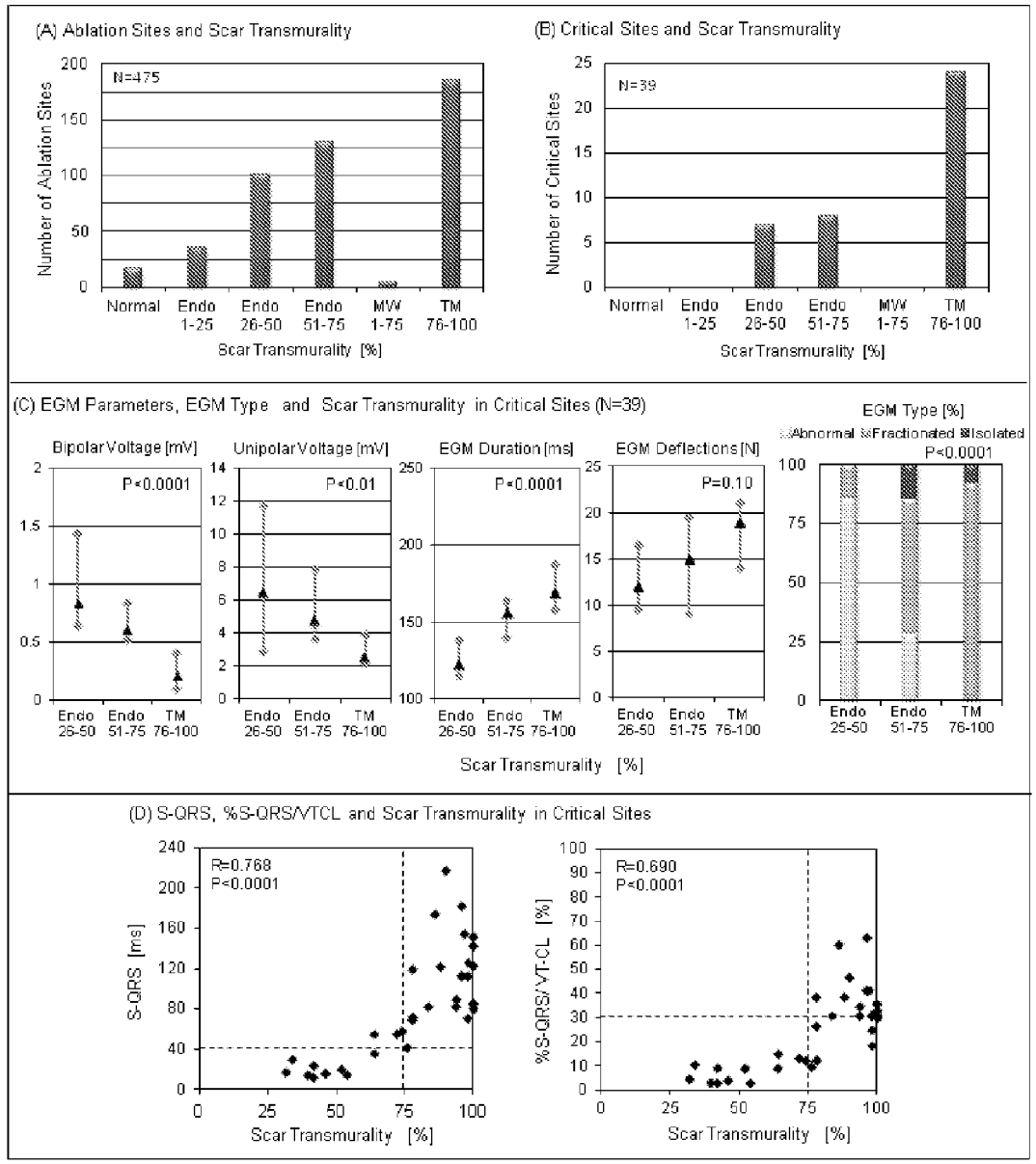
FIGS. 4A-4D illustrate the association of ablation sites and critical sites of reentrant VT with scar transmurality. (A) Ablation sites were observed in regions with scar and normal myocardium adjacent to the scar. (B) The critical sites were identified only in scar region with endocardial 26-75% and transmural 76-100% scar transmurality. (C) Significant associations among EGM parameters and EGM types with scar transmurality were observed (except EGM deflections) within critical sites. (D) S-QRS ($R=0.768$, $P<0.0001$) and % S-QRS/VT-CL ($R=0.690$, $P<0.0001$) were significantly associated with scar transmurality. (R). The critical sites with $\geq 40$ ms of S-QRS and $\geq 30\%$ of % S-QRS/VT-CL were identified by 75% scar transmurality with 89.7% sensitivity and 100% specificity, 100% sensitivity and 65% specificity, respectively.

A total of 475 radiofrequency applications were delivered. Of all lesions, 7.6%, 21.3%, 27.4%, and 39.1% were delivered to areas with endocardial 1-25%, 26-50%, 51-75%, and 76-100% scar transmurality, respectively (FIG. 4A). In addition, 1.0% and 3.9% were delivered to regions with mid wall scar and no enhancement but adjacent to scar as determined by LGE-CMR. A total of 39 critical sites of reentrant VT were identified and correlated to the corresponding LGE-CMR images. Of all critical sites, 17.9%, 20.5% and 61.5% were identified in regions with 26-50% [range: 32-46%], 51-75% [52-74%], and 76-100% [76-100%] scar transmurality, respectively (FIG. 4B). The mean scar transmurality in sectors corresponding to VT critical sites was 73±21%. Of all critical sites, 23 sites (59%) were located within 10 mm of the scar border with less than 25% scar transmurality on LGE-CMR, and the remaining 44% were in the scar core.[19] Significant associations were also observed between EGM parameters and EGM types with scar transmurality within critical sites (FIG. 4C). S-QRS and % S-QRS/VT-CL were significantly associated with scar transmurality (P<0.0001, respectively; FIG. 4D). The critical sites with ≤40 msec of S-QRS delay were identified by 75% scar transmurality with 89.7% sensitivity and 100% specificity. The critical sites with 30% of % S-QRS/VT were also identified by 75% scar transmurality with sensitivity 100% and specificity 65%.

Independent Predictors of EGM Parameters by Multi-level Multivariate Linear Regression Analysis Multi-level multivariate linear regression analysis results with EGM parameters as dependent variables and LGE-CMR variables as independent variables have been summarized in Table 3. LV-WT and PI-ST remained independently associated with each EGM parameter (P<0.001, for both). There were also significant associations between myocardial location with bipolar EGM voltage (P<0.001), intramural scar location with EGM duration (P<0.001); and intramural scar location, age, LV ejection fraction and use of antiarrhythmic drug with EGM deflections (P<0.05, for all variables).

TABLE 3

Multivariate Multi-Level Linear Regression Analysis

| | Electrogram Parameters | | | | | | | |
| --- | --- | --- | --- | --- | --- | --- | --- | --- |
| | Bipolar Voltage (mV) | | Unipolar Voltage (mV) | | Duration (msec) | | Deflections (number) | |
| Independent Variables | B | P | B | P | B | P | B | P |
| LV Wall Thickness (mm) | 0.363 | <0.001* | 0.692 | <0.001* | −3.570 | <0.001* | −0.819 | <0.001* |
| Post-infarct Scar Thickness (mm) | −0.395 | <0.001* | −0.610 | <0.001* | 4.558 | <0.001* | 0.542 | <0.001* |

TABLE 3-continued

Multivariate Multi-Level Linear Regression Analysis

| Independent Variables | Bipolar Voltage (mV) | | Unipolar Voltage (mV) | | Duration (msec) | | Deflections (number) | |
|---|---|---|---|---|---|---|---|---|
| | B | P | B | P | B | P | B | P |
| Myocardial Location (Anterior, Septal, inferior, Lateral) | 0.283 | <0.001* | 0.054 | 0.583 | 0.992 | 0.241 | 0.172 | 0.147 |
| Intramural Scar Location (Endocardial, Mid Wall, Transmural) | 0.043 | 0.642 | −0.022 | 0.903 | 8.573 | <0.001* | 0.661 | 0.004* |
| Age (years) | −0.021 | 0.411 | 0.026 | 0.680 | 0.383 | 0.641 | 0.281 | 0.031* |
| Body Mass Index (kg/m2) | −0.025 | 0.475 | 0.023 | 0.767 | −0.411 | 0.721 | 0.295 | 0.109 |
| LV Ejection Fraction (%) | 0.015 | 0.423 | 0.034 | 0.462 | −0.201 | 0.745 | −0.215 | 0.030* |
| History of CABG | −0.428 | 0.281 | −1.238 | 0.208 | 7.415 | 0.578 | 1.360 | 0.524 |
| Antiarrhythmic Drug Use (Amiodarone, Sotalol) | −0.169 | 0.582 | −1.378 | 0.073 | 20.40 | 0.053 | 4.338 | 0.011* |

Significant regression coefficients and P-values defined as P < 0.05 are shown by asterisks (*).
B = regression coefficients; P = P-value. See abbreviations in Table 1.

Non-Invasive Creation of 3D Substrate Maps Based on LGE-CMR

Figure 5:
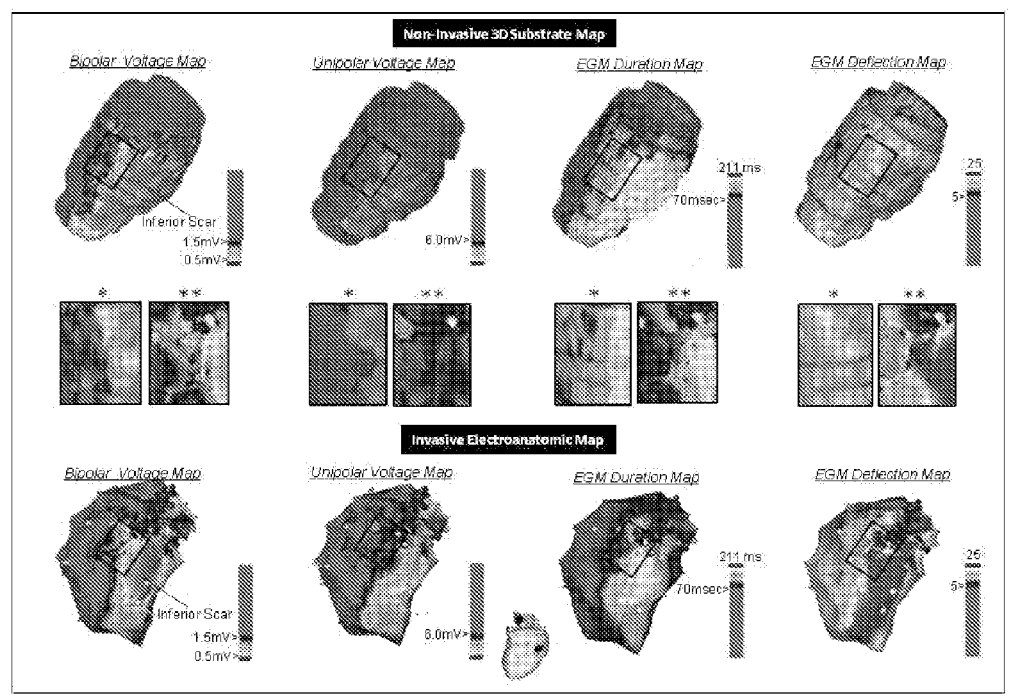
FIG. 5 is an illustration of a qualitative comparison of prospective non-invasive 3D substrate maps predicted based on LGE-CMR images, versus invasive maps in a patient with inferior myocardial infarction. Upper panel: Non-invasive 3D substrate maps for bipolar and unipolar EGM voltage, duration and deflections. The maps were constructed prior to the procedure by custom software using LV-WT and PIST on LGE-CMR and the coefficients derived from training set multivariate analyses. Middle panel: Higher resolution qualitative comparison of non-invasive map with invasive maps in a part of the LV. The resolution of the noninvasive maps ($1.5 \times 1.2 \times 8$ mm) was higher than that of invasive maps obtained by point-by-point mapping; therefore, minute differences in image characteristics of the predicted map versus the invasive map may be due to extrapolation of each "real" electrogram to nearby areas on the invasive map (for quantitative comparison of predicted EGM parameters to invasive measures please see FIG. 6). Lower panel: Invasive EAMs of bipolar and unipolar voltage, duration and deflection and ablation points (red points). The EAM system does not provide duration and deflection maps routinely, the invasive duration and deflection measures were manually entered for each 3-dimensional location for color display and comparison to the predicted maps.
Figures 6A, 6B, 6C, 6D:
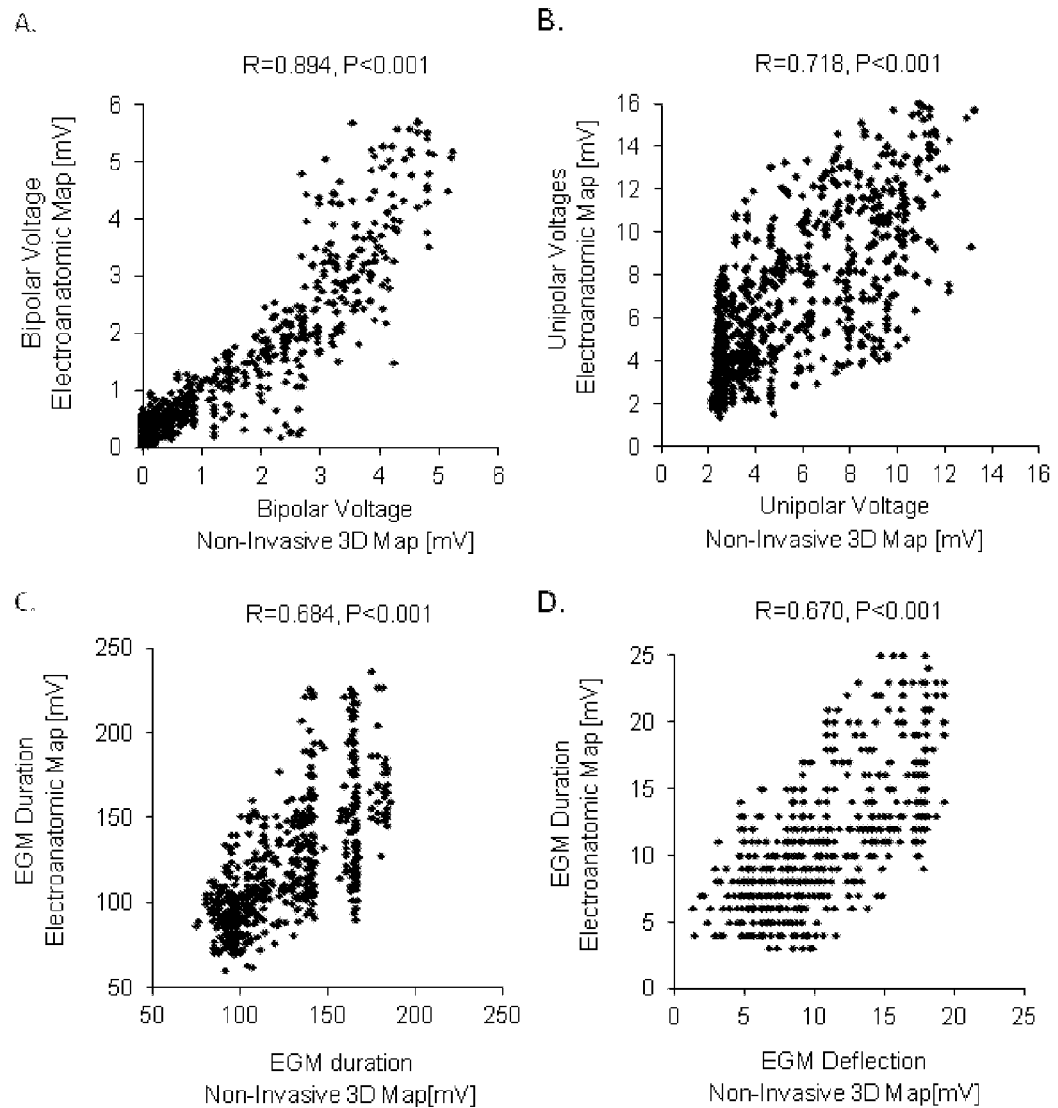
FIGS. 6A-6D show that there were significant associations in each EGM parameters such as bipolar and unipolar EGM amplitudes, EGM duration and EGM deflections between the prospective estimates on non-invasive 3D maps and the invasive measures on electroanatomic maps (A-D; $P<0.0001$. respectively)

In the test series, non-invasive 3D substrate maps of EGM bipolar and unipolar voltage, duration, and deflections were successfully created using variables and coefficients derived from multivariate linear regression analyses of the retrospective training set (FIG. 5). Spearman's correlation test revealed a significant association between the invasively measured EGM variables and non-invasive magnetic resonance based estimates of local bipolar (R=0.894, P<0.0001) and unipolar voltage amplitudes (R=0.718, P<0.0001), duration (R=0.684, P<0.0001) and deflections (R=0.670, P<0.0001) (FIG. 6).

Discussion

The main finding of this example is that after adjusting for patient characteristics, scar thickness and viable myocardium thickness are significantly associated with local intra-cardiac bipolar and unipolar EGM voltage, duration and deflections in patients with ischemic cardiomyopathy. Accurate non-invasive 3D substrate maps can be successfully created using multivariate regression models that summarize the associations between scar on LGE-CMR and EGM parameters on invasive EAM. Additionally, critical sites necessary for initiation and maintenance of VT were located in areas with >25% scar transmurality and central pathway sites were located in areas with >75% scar transmurality on LGE-CMR.

LV-WT and PI-ST as Independent Predictors of Each EGM Parameter

Previous reports have described significant associations between scar thickness identified by LGE-CMR[14-19], pathology[8,20,21] or PET-CT[22] and local bipolar and/or unipolar EGM voltage.[14-16,20] It is biologically accepted that viable myocardial tissue rather than scar produces the electrical characteristics in each myocardial region. However, previous reports have primarily focused on scar thickness or the ratio of scar to viable tissue rather than LV-WT and PI-ST as independent variables. In our study, cine-CMR images obtained by the steady state free precession sequence were essential to accurately determine LV-WT on each short axis plane (FIG. 2A). Multi-level (clustered by patient) multivariate linear regression analyses (Table 3) elucidated the independent significance of LV-WT and PI-ST as predictors of EGM signal characteristics. Our study also demonstrated that myocardial location is a significant determinant of bipolar but not unipolar EGM voltage. In contrast, the intramural scar location was a primary determinant of EGM duration and deflections and not bipolar or unipolar voltage. Most interestingly, the number of EGM deflections was significantly associated with age, LV ejection fraction, and antiarrhythmic drug use. This novel finding suggests that EGM deflections as a surrogate of slow conduction is affected not only by LV-WT and PI-ST but also by other patient characteristics that contribute to slow myocardial conduction.

Scar Transmurality and EGM Characteristics

Wolf et al.[20] demonstrated a significant association between scar transmurality and bipolar EGM voltage by regression analysis using EAM data (263 EAM points) in 13 dogs with infarct scar. We analyzed a total of 2093 EAM points and showed a similar association between scar transmurality and EGM characteristics in human myocardium. The positive association between EGM duration and deflections with scar transmurality suggests the existence of slow conduction in regions with higher scar transmurality. In addition, fractionated EGM and isolated potentials are directly associated with scar transmurality and critical sites of scar-related VT were confined to regions with scar. Interestingly, the mean bipolar voltage of areas without delayed enhancement was lower, and EGM duration longer, when compared to results obtained from normal myocardium patients without structural heart disease (3.0±2.3 mV and 96.5±27.0 ms respectively in our study, versus 6.7±3.4 mV and 54±13 ms, respectively in patients without structural heart disease). This finding, which is consistent with EAM results from Desjardins et al and Condreanu et al,[15,17] suggests that even "normal" areas without evidence of scar exhibit slight alterations in electrophysiologic properties in patients with chronic ischemic cardiomyopathy.

Scar Transmurality and Critical Sites of Scar-Related Reentrant VT

Previous reports have revealed EGM characteristics in critical sites necessary for VT initiation and maintenance.[1-9] Here we report a significant association of critical site location with scar transmurality >25%. In addition, >75% scar transmurality was significantly associated with >40 msec of S-QRS[1,3,4] and >30% of % S-QRS/VTCL.[1,2] Thus, slow conduction in central pathways of VT circuits appear to be associated with scar regions with >75% scar transmurality. Additionally, exit sites are associated with infarct scar with 25-75% scar transmurality.

Non-Invasive 3-Dimensional Substrate Maps Based on LGE-CMR

Based upon multivariate linear regression analyses on the training set, left ventricular wall thickness and scar thickness on LGE-CMR were utilized to prospectively predict EGM characteristics in patients in the test set. While, all EGM parameters were predicted with reasonable accuracy compared to invasive mapping, bipolar voltage was predicted with excellent calibration and discrimination properties. Importantly, bipolar voltage maps are the most important method used for substrate mapping in ischemic cardiomyopathy. Due to the limited sampling density of endocardial invasive mapping, non-invasive 3D bipolar voltage maps as proposed and demonstrated in this study have the capacity to be more reflective of the true underlying substrate. Additionally, non-invasive creation of 3D duration and deflection maps have the capacity to provide additional information not currently provided using standard EAM software, and will likely reduce procedural and fluoroscopy time devoted to substrate identification. Importantly, the patients in this study had ischemic cardiomyopathy, severe LV dysfunction, and ICDs prior to ablation procedures; and therefore, the data is generalizable to typical patients referred for catheter ablation of VT.

CONCLUSIONS

LV-WT and PI-ST on LGE-CMR of patients with ischemic cardiomyopathy were independently and significantly associated with local intra-cardiac bipolar and unipolar EGM voltage, duration and deflections. These associations enable the creation of non-invasive CMR based substrate maps prior to VT ablation. This novel methodology may improve the safety and efficacy of catheter ablation in patients with ischemic scar-related VT by providing a summary of image details directly useful to the electrophysiologist, reducing procedural time, and mitigating sampling density limitations.

REFERENCES

1. Stevenson W G, Khan H, Sager P, Saxon L A, Middlekauff H R, Natterson P D, Wiener I. Identification of reentry circuit sites during catheter mapping and radiofrequency ablation of ventricular tachycardia late after myocardial infarction. *Circulation.* 1993; 88:1647-70.
2. Hsia H H, Lin D, Sauer W H, Callans D J, Marchlinski F E. Anatomic characterization of endocardial substrate for hemodynamically stable reentrant ventricular tachycardia: Identification of endocardial conducting channels. Heart Rhythm 2006; 3:503-512.
3. Brunckhorst C B, Stevenson W G, Soejima K, Maisel W H, Delacretaz E, Friedman P L, Ben-Haim S A. Relationship of Slow Conduction Detected by Pace-Mapping to Ventricular Tachycardia Re-Entry Circuit Sties After Infarction. J Am Coll Cardiol. 2003; 41:802-809.
4. Stevenson W G, Spager P T, Natterson P D, Saxon L A, Middlekauff H R, Wiener I. Relation of pace mapping QRS configuration and conduction delay to ventricular tachycardia reentry circuits in human infarct scars. J Am Coll Cardiol 1995; 26:481-488.
5. Chillou C D, Lacroix D, Klug D, Magnin-Poull I, Marquie C, Messier M, Andronache M, Kouakam C, Sadoul N, Chen J, Aliot E, Kacet S. Isthmus characteristics of reentrant ventricular tachycardia aftere myocardial infarction. Circulation. 2002; 105:726-731.
6. Bogun F, Good E, Reich S, Elmouchi D, Igic P, Lemola K, Tschopp D, Jongnarangsin K, Oral H Chugh A, Pelosi F, Morady F. Isolated potentials during sinus rhythm and pace-mapping within scars as guides for ablation of post-infarction ventricular tachycardia. *J Am Coll Cardiol.* 2006; 47:2013-2019.
7. Estner H L, Zviman M M, Herzka D, Miller F, Castro V, Nazarian S, Ashikaga H, Dori Y, Berger R D, Calkins H, Lardo A C, Halperin H R. The critical isthmus sites of ischemic ventricular tachycardia are in zones of tissue heterogeneity, visualized by magnetic resonance imaging. Heart Rhythm. 2011; 8:1942-1949.
8. Perez-David E, Arenal A, Rubio-Guivernau J L, del Castillo R, Atea L, Arbelo E, Caballero E, Celorrio V, Datino T, Gonzalez-Torrecilla E, Atienza F, Ledesma-Carbayo M J, Bermejo J, Medina A, Fernández-Avilés F. Non-invasive identification of ventricular tachycardia-related conducting channels using contrast-enhanced magnetic resonance imaging in patients with chronic myocardial infarction: comparison of signal intensity scar mapping and endocardial voltage mapping. J Am Coll Cardiol. 2011; 57:184-194.
9. Marchlinski F E, Callans D J, Gottlieb C D, Zado E. Linear ablation lesions for control of unmappable ventricular tachycardia in patients with ischemic and nonischemic cardiomyopathy. Circulation. 2000; 101:1288-1296.
10. Kim R J, Fieno D S, Parrish T B, Harris K. Chen E L. Simonetti O, Bundy J, Finn J P, Klocke F J, Judd R M. Relationship of MRI delayed contrast enhancement to irreversible injury, infarct age, and contractile function. Circulation. 1999; 100:1992-2002.
11. Setser R M, Bexell D G, O'Donnell T P, Stillman A E, Lieber M L, Schoenhagen P, White R D. Quantitative assessment of myocardial scar in delayed enhancement magnetic resonance imaging. *J Magn Reson Imaging.* 2003; 18:434-441.
12. Roes S D. Borleffs C J, van der Geest R J, Westenberg J J, Marsan N A, Kaandorp T A, Reiber J H, Zeppenfeld K, Lamb H J, de Roos A, Schalij M J, Bax J J. Infarct tissue heterogeneity assessed with contrast-enhanced MRI predicts spontaneous ventricular arrhythmia in patients with ischemic cardiomyopathy and implantable cardioverter-defibrillator. *Circ Cardiovasc Imaging.* 2009; 2:183-190.
13. Nazarian S, Bluemke D A, Lardo A C, Zviman M M, Watkins S P, Dickfeld T L, Meininger G R, Roguin A, Calkins H, Tomaselli G F, Weiss R G, Berger R D, Lima J A, Halperin H R. Magnetic resonance assessment of the substrate for inducible ventricular tachycardia in nonischemic cardiomyopathy. *Circulation.* 2005; 112:2821-5.
14. Perin E C, Silva G V, Sarmento-Leite R, Sousa A L, Howell M, Muthupillai R, Lambert B, Vaughn W K, Flamm S D. Assessing myocardial viability and infarct transmurality with left ventricular electromechanical mapping in patients with stable coronary artery disease: validation by delayed-enhancement magnetic resonance imaging. *Circulation.* 2002; 106:957-961.

15. Codreanu A, Odille F, Aliot E, Marie P Y, Magnin-Poull I, Andronache M, Mandry D, Djaballah W, Régent D, Felblinger J, de Chillou C. Electroanatomic characterization of post-infarct scars comparison with 3-dimensional myocardial scar reconstruction based on magnetic resonance imaging. *J Am Coll Cardiol.* 2008; 52:839-842.

16. Wijnmaalen A P, van der Geest R J, van Huls van Taxis C F, Siebelink H M, Kroft L J, Bax J J, Reiber J H, Schalij M J, Zeppenfeld K. Head-to-head comparison of contrast-enhanced magnetic resonance imaging and electroanatomical voltage mapping to assess post-infarct scar characteristics in patients with ventricular tachycardias: real-time image integration and reversed registration. *Eur Heart J.* 2011; 32:104-114.

17. Desjardins B, Crawford T, Good E, Oral H, Chugh A, Pelosi F, Morady F, Bogun F. Infarct architecture and characteristics on delayed enhanced magnetic resonance imaging and electroanatomic mapping in patients with postinfarction ventricular arrhythmia. *Heart Rhythm.* 2009; 6:644-651.

18. Psaltis P J, Carbone A, Leong D P, Lau D H, Nelson A J, Kuchel T, Jantzen T, Manavis J, Williams K, Sanders P, Gronthos S, Zannettino A C, Worthley S G. Assessment of myocardial fibrosis by endoventricular electromechanical mapping in experimental nonischemic cardiomyopathy. *Int J Cardiovasc Imaging.* 2011; 27:25-37.

19. Dickfeld T, Tian J, Ahmad G, Jimenez A, Turgeman A, Kuk R, Peters M, Saliaris A, Saba M, Shorofsky S, Jeudy J. MRI-Guided Ventricular Tachycardia Ablation: Integration of Late Gadolinium-Enhanced 3D Scar in Patients With Implantable Cardioverter-Defibrillators. *Circ Arrhythm Electrophysiol.* 2011; 4:172-184.

20. Wolf T, Gepstein L, Dror U, Hayam G, Shofti R, Zaretzky A, Uretzky G, Oron U, Ben-Haim S A. Detailed endocardial mapping accurately predicts the transmural extent of myocardial infarction. *J Am Coll Cardiol.* 2001; 37:1590-1597.

21. Reddy V Y, Wrobleski D, Houghtaling C, Josephson M E, Ruskin J N. Combined epicardial and endocardial electroanatomic mapping in a porcine model of healed myocardial infarction. *Circulation.* 2003; 107:3236-3242.

22. Dickfeld T, Lei P, Dilsizian V, Jeudy J, Dong J, Voudouris A, Peters R, Saba M, Shekhar R, Shorofsky S. Integration of three-dimensional scar maps for ventricular tachycardia ablation with positron emission tomography-computed tomography. *JACC Cardiovasc Imaging.* 2008; 1:73-82.

23. Nazarian S. Roguin A, Zviman M M, Lardo A C, Dickfeld T L, Calkins H, Weiss R G, Berger R D, Bluemke D A, Halperin H R. Clinical utility and safety of a protocol for noncardiac and cardiac magnetic resonance imaging of patients with permanent pacemakers and implantable-cardioverter defibrillators at 1.5 tesla. Circulation. 2006; 114:1277-1284.

24. Nazarian S, Hansford R, Roguin A, Goldsher D, Zviman M M, Lardo A C, Caffo B S, Frick K D, Kraut M A, Kamel I R, Calkins H, Berger R D, Bluemke D A, Halperin H R. A prospective evaluation of a protocol for magnetic resonance imaging of patients with implanted cardiac devices. Ann Intern Med. 2011; 155:415-24.

25. Sasaki T, Hansford R, Zviman M M, Kolandaivelu A, Bluemke D A, Berger R D, Calkins H, Halperin H R, Nazarian S. Quantitative assessment of artifacts on cardiac magnetic resonance imaging of patients with pacemakers and implantable cardioverter-defibrillators. Circ Cardiovasc Imaging. 2011; 4:662-70.

26. Bertaglia E, Brandolino G, Zoppo F, Zerbo F, Pascotto P. Integration of three-dimensional left atrial magnetic resonance images into a real-time electroanatomic mapping system: validation of a registration method. Pacing Clin Electrophysiol. 2008; 31:273-282.

27. Tung R, Nakahara S, Ramirez R, Lai C, Fishbein M C, Shivkumar K. Distinguishing epicardial fat from scar: Analysis of electrograms using high-density electroanatomic mapping in a novel porcine infarct model. Heart Rhythm. 2010; 7:389-395.

28. Zeppenfeld K, Kiès P, Wijffels M C, Bootsma M, van Erven L, Schalij M J. Identification of successful catheter ablation sites in patients with ventricular tachycardia based on electrogram characteristics during sinus rhythm. *Heart Rhythm.* 2005; 2:940-50.

29. Josephson M. Clinical Cardiac Electrophysiology Techniques and Interpretations, 3rd ed. Lippincott Williams & Wilkins, Philadelphia 2002.

30. Otomo K, Uno K, Fujiwara H, Isobe M, Iesaka Y. Local unipolar and bipolar electrogram criteria for evaluating the transmurality of atrial ablation lesions at different catheter orientation relative to the endocardial surface. Heart Rhythm. 2010; 7:1291-1300.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A non-invasive method of producing a three-dimensional cardiac electrogram characteristic map for use in catheter ablation of ventricular tachycardia, comprising:
    receiving left ventricle three-dimensional image data of a patient's heart;
    segmenting a left ventricle image of said patient's heart based on said left ventricle three-dimensional image data into scar tissue, normal myocardium tissue and left ventricle cavity regions;
    determining scar tissue thickness and normal myocardium tissue thickness for a plurality of portions of said left ventricle image of said patient's heart;
    receiving predetermined data that associate a value of at least one electrogram characteristic to each scar tissue thickness and each normal myocardium tissue thickness for said plurality of portions of said left ventricle image of said patient's heart; and
    generating said three-dimensional cardiac electrogram characteristic map of said at least one electrogram characteristic corresponding to said left ventricle image of said patient's heart based on said predetermined data.

2. The method of claim 1, wherein said at least one electrogram characteristic is at least one of bipolar voltage amplitude, unipolar voltage amplitude, electrogram deflection, electrogram fractionation, or electrogram duration.

3. The method of claim 1, further comprising receiving patient characteristic data,
    wherein said generating said three-dimensional cardiac electrogram characteristic map is further based on said patient characteristic data.

4. The method of claim 3, wherein said patient characteristic data comprises at least one of age, gender, body mass index, history of coronary artery bypass grafting, or history of use of antiarrhythmic drugs.

5. The method of claim 3, further comprising determining left ventricle fraction ejection of said patient based on said left ventricle three-dimensional image data,
wherein said patient characteristic data comprises said left ventricle fraction ejection.

6. The method of claim 1, wherein said predetermined data are empirically determined.

7. The method of claim 6, wherein said predetermined data are empirically determined based on a multi-level, multivariate linear regression analysis of empirical data.

8. The method of claim 1, wherein said receiving left ventricle three-dimensional image data is receiving magnetic resonance image (MRI) data.

9. The method of claim 1, wherein said MRI data is late gadolinium enhancement on cardiac magnetic resonance data.

10. A non-transitory computer-readable medium comprising computer-executable code for producing a three-dimensional cardiac electrogram characteristic map for use in catheter ablation of ventricular tachycardia, said computer-executable code comprising instructions that, when executed by said computer, causes said computer to:
receive left ventricle three-dimensional image data of a patient's heart;
segment a left ventricle image of said patient's heart based on said left ventricle three-dimensional image data into scar tissue, normal myocardium tissue and left ventricle cavity regions;
determine scar tissue thickness and normal myocardium tissue thickness for a plurality of portions of said left ventricle image of said patient's heart;
receive predetermined data that associate a value of at least one electrogram characteristic to each scar tissue thickness and each normal myocardium tissue thickness for said plurality of portions of said left ventricle image of said patient's heart; and
render a three-dimensional cardiac electrogram characteristic map of said at least one electrogram characteristic corresponding to said left ventricle image of said patient's heart based on said predetermined data.

11. The non-transitory computer-readable medium of claim 10, wherein said at least one electrogram characteristic is at least one of bipolar voltage amplitude, unipolar voltage amplitude, electrogram deflection, electrogram fractionation, or electrogram duration.

12. The non-transitory computer-readable medium of claim 10, wherein said non-transitory computer-executable code further comprises instructions that, when executed by said computer, causes said computer to receive patient characteristic data,
wherein said rendering said three-dimensional cardiac electrogram characteristic map is further based on said patient characteristic data.

13. The non-transitory computer-readable medium of claim 12, wherein said patient characteristic data comprises at least one of age, gender, body mass index, history of coronary artery bypass grafting, or history of use of antiarrhythmic drugs.

14. The non-transitory computer-readable medium of claim 12, wherein said non-transitory computer-executable code further comprises instructions that, when executed by said computer, causes said computer to determine left ventricle fraction ejection of said patient based on said left ventricle three-dimensional image data,
wherein said patient characteristic data comprises said left ventricle fraction ejection.

15. The non-transitory computer-readable medium of claim 10, wherein said predetermined data are empirically determined.

16. The non-transitory computer-readable medium of claim 15, wherein said predetermined data are empirically determined based on a multi-level, multivariate linear regression analysis of empirical data.

17. The non-transitory computer-readable medium of claim 10, wherein said left ventricle three-dimensional image data is magnetic resonance image (MRI) data.

18. The non-transitory computer-readable medium of claim 10, wherein said MRI data is late gadolinium enhancement on cardiac magnetic resonance data.

19. A system for producing a three-dimensional cardiac electrogram characteristic map for use in catheter ablation of ventricular tachycardia, comprising:
a data processing unit; and
a data storage unit configured to communicate with said data storage unit,
wherein said data processing unit is configured to execute instructions that causes said system to:
receive left ventricle three-dimensional image data of a patient's heart;
segment a left ventricle image of said patient's heart based on said left ventricle three-dimensional image data into scar tissue, normal myocardium tissue and left ventricle cavity regions;
determine scar tissue thickness and normal myocardium tissue thickness for a plurality of portions of said left ventricle image of said patient's heart;
receive predetermined data that associate a value of at least one electrogram characteristic to each scar tissue thickness and each normal myocardium tissue thickness for said plurality of portions of said left ventricle image of said patient's heart; and
render a three-dimensional cardiac electrogram characteristic map of said at least one electrogram characteristic corresponding to said left ventricle image of said patient's heart based on said predetermined data.

20. The system of claim 19, wherein said at least one electrogram characteristic is at least one of bipolar voltage amplitude, unipolar voltage amplitude, electrogram deflection, electrogram fractionation, or electrogram duration.

21. The system of claim 19, wherein said data processing unit is configured to execute instructions that causes said system to receive patient characteristic data,
wherein said rendering said three-dimensional cardiac electrogram characteristic map is further based on said patient characteristic data.

22. The system of claim 21, wherein said patient characteristic data comprises at least one of age, gender, body mass index, history of coronary artery bypass grafting, or history of use of antiarrhythmic drugs.

23. The system of claim 21, wherein said data processing unit is further configured to execute instructions that causes said system to determine left ventricle fraction ejection of said patient based on said left ventricle three-dimensional image data,
wherein said patient characteristic data comprises said left ventricle fraction ejection.

24. The system of claim 19, wherein said predetermined data are empirically determined.

25. The system of claim 24, wherein said predetermined data are empirically determined based on a multi-level, multivariate linear regression analysis of empirical data.

26. The system of claim 19, wherein said left ventricle three-dimensional image data is magnetic resonance image (MRI) data.

27. The system of claim 19, wherein said MRI data is late gadolinium enhancement on cardiac magnetic resonance data.

\* \* \* \* \*